(12) United States Patent
Cory et al.

(10) Patent No.: US 6,564,079 B1
(45) Date of Patent: *May 13, 2003

(54) ELECTRODE ARRAY AND SKIN ATTACHMENT SYSTEM FOR NONINVASIVE NERVE LOCATION AND IMAGING DEVICE

(75) Inventors: Philip C. Cory, Bozeman, MT (US); Joan M. Cory, Bozeman, MT (US)

(73) Assignee: CKM Diagnostics, Inc., Bozeman, MO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 109 days.

(21) Appl. No.: 09/624,397

(22) Filed: Jul. 27, 2000

(51) Int. Cl.⁷ .................................................. A61B 5/04
(52) U.S. Cl. ................... 600/393; 600/395; 600/397; 600/547; 600/554; 607/152
(58) Field of Search .............................. 600/547, 548, 600/554, 557, 382, 386, 391, 393, 397, 395; 607/152, 46, 118; 33/512

(56) References Cited

U.S. PATENT DOCUMENTS

| | | |
|---|---|---|
| 2,008,295 A | 7/1935 | Smith |
| 2,018,080 A | 10/1935 | Martienssen |
| 2,298,506 A | 10/1942 | Parker et al. |
| 2,704,064 A | 3/1955 | Fizzell et al. |
| 3,078,850 A | 2/1963 | Schein et al. |
| 3,612,060 A | 10/1971 | Colyer |
| 3,612,061 A | 10/1971 | Collins |
| 3,624,484 A | 11/1971 | Colyer |
| 3,664,329 A | 5/1972 | Naylor |
| 3,682,162 A | 8/1972 | Colyer |
| 3,830,226 A | 8/1974 | Staub et al. |
| 3,954,100 A | 5/1976 | Sem-Jacobsen |
| 3,989,051 A | 11/1976 | Nozhnikov et al. |
| 4,016,870 A | 4/1977 | Lock ........................ 128/2.1 C |

(List continued on next page.)

OTHER PUBLICATIONS

Arthur L. Kaslow, et al., "Dragon Chasing: A New Technique for Acupuncture Point Finding and Stimulation", American Journal Acupuncture, vol. 3, No. 2, Apr.–Jun. 1975.

G. Kwok et al., "Mapping Acupunture Points Using Multi Channel Device", Australasian Physical and Engineering Sciences in Medicine, vol. 21, No. 2, 1998.

David T. Lykken, Square–Wave Analysis of Skin Impedance, Psychophysiology, 7(2):262–275,1971.

Maria Reichmanis et al., Electrical Correlates of Acupuncture Points, IEEE Transactions on Biomedical Engineering, BME, 22:533–535, 1975.

J. Jossinet and E. McAdams, Hydrogel Electrodes in Bio–signal Recording, Annual International Conference on the IEEE Engineering in Medicine and Biology Society, 12(4):1490–1491, 1990.

Kejariwal et al., "Development of a Device for Non–Invasive Nerve Location", Abstracts, 8th World Congress on Pain, Vancouver, British Columbia, Canada, Aug. 17–22, 1996.

*Primary Examiner*—Linda C. M. Dvorak
*Assistant Examiner*—David M. Ruddy
(74) *Attorney, Agent, or Firm*—McDermott, Will & Emery (57) ABSTRACT

A system for detecting and marking the positions of peripheral nerves is disclosed. A reusable electrode array comprising a plurality of electrodes is combined with a disposable skin attachment system comprising hydrogel islands. In use, the electrode array is connected to a peripheral nerve detection instrument. The disposable skin attachment system is then attached to an electrode sensor region. The skin attachment system is then adhered to an area of skin, detection is carried out, and then the electrode array is peeled back from the skin, leaving a skin marking guide in place. The skin marking guide is then used to mark areas of interest to a therapist.

21 Claims, 7 Drawing Sheets

U.S. PATENT DOCUMENTS

| | | |
|---|---|---|
| 4,157,087 A | 6/1979 | Miller et al. |
| 4,257,424 A | 3/1981 | Cartmell |
| 4,334,542 A | 6/1982 | Takinishi et al. |
| 4,370,984 A | 2/1983 | Cartmell |
| 4,390,023 A | 6/1983 | Rise |
| 4,408,617 A | 10/1983 | Auguste |
| 4,459,995 A | 7/1984 | Conners et al. |
| 4,461,304 A | 7/1984 | Kuperstein |
| 4,486,835 A | 12/1984 | Bai et al. |
| 4,515,168 A | 5/1985 | Chester et al. |
| 4,539,640 A | 9/1985 | Fry et al. |
| 4,540,002 A | 9/1985 | Atlas |
| 4,557,271 A | 12/1985 | Stoller et al. |
| 4,578,635 A | 3/1986 | Mee et al. |
| 4,595,013 A | 6/1986 | Jones et al. |
| 4,616,660 A | 10/1986 | Johns |
| 4,619,266 A | 10/1986 | Hodgson |
| 4,630,615 A | 12/1986 | Yomtov |
| 4,633,889 A | 1/1987 | Talalla et al. |
| 4,635,641 A | 1/1987 | Hoffman |
| 4,649,932 A | 3/1987 | Smith |
| 4,685,467 A | 8/1987 | Cartmell et al. |
| 4,702,259 A | 10/1987 | Ferreire et al. |
| 4,753,246 A | 6/1988 | Freeman |
| 4,763,660 A | 8/1988 | Kroll et al. |
| 4,794,934 A | 1/1989 | Motoyama et al. |
| 4,805,621 A | 2/1989 | Heinze et al. |
| 4,807,638 A | 2/1989 | Sramek |
| 4,823,797 A | 4/1989 | Heinze et al. |
| 4,836,214 A | 6/1989 | Sramek |
| 4,838,273 A | 6/1989 | Cartmell |
| 4,892,105 A | 1/1990 | Prass |
| 4,917,093 A | 4/1990 | Dufresne et al. |
| 4,926,865 A | 5/1990 | Oman |
| 4,962,766 A | 10/1990 | Herzon |
| 4,969,468 A | 11/1990 | Byers et al. |
| 5,010,896 A | 4/1991 | Westbrook |
| 5,044,368 A | 9/1991 | Putz |
| 5,058,605 A | 10/1991 | Slovak |
| 5,063,937 A | 11/1991 | Ezenwa et al. |
| 5,067,953 A | 11/1991 | Feucht |
| 5,092,332 A | 3/1992 | Lee et al. |
| 5,092,344 A | 3/1992 | Lee |
| 5,150,708 A | 9/1992 | Brooks |
| 5,199,432 A | 4/1993 | Quedens et al. |
| 5,203,344 A | 4/1993 | Scheltinga et al. |
| 5,215,100 A | 6/1993 | Spitz et al. |
| 5,272,624 A | 12/1993 | Gisser et al. |
| 5,284,153 A | 2/1994 | Raymond et al. |
| 5,284,154 A | 2/1994 | Raymond et al. |
| 5,295,482 A | 3/1994 | Clare et al. |
| 5,305,746 A | 4/1994 | Fendrock |
| 5,335,668 A | 8/1994 | Nardella |
| 5,353,802 A | 10/1994 | Ollmar |
| 5,356,428 A | 10/1994 | Way |
| 5,361,762 A | 11/1994 | Gunter |
| 5,366,497 A | 11/1994 | Ilvento et al. |
| 5,385,150 A | 1/1995 | Ishikawa |
| 5,388,577 A | 2/1995 | Hubbard |
| 5,397,344 A | 3/1995 | Garfield et al. |
| 5,427,098 A | 6/1995 | Faupel et al. |
| 5,443,486 A | 8/1995 | Hrdlicka et al. |
| 5,449,378 A | 9/1995 | Schouenborg |
| 5,501,230 A | 3/1996 | Laribiere |
| 5,503,157 A | 4/1996 | Sramek |
| 5,522,877 A | 6/1996 | Garfield et al. |
| 5,529,072 A | 6/1996 | Sramek |
| 5,534,003 A | 7/1996 | Cole |
| 5,560,372 A | 10/1996 | Cory ............................ 128/741 |
| 5,563,067 A | 10/1996 | Sugihara et al. |
| 5,626,575 A | 5/1997 | Crenner |
| 5,642,734 A | 7/1997 | Ruben et al. |
| 5,645,063 A | 7/1997 | Straka, Jr. |
| 5,715,821 A | 2/1998 | Faupel |
| 5,720,296 A | 2/1998 | Cha |
| 5,733,151 A * | 3/1998 | Edsall et al. ................. 439/909 |
| 5,772,591 A | 6/1998 | Cram |
| 5,775,331 A | 7/1998 | Raymond et al. |
| 5,779,642 A | 7/1998 | Nightengale |
| 5,782,238 A | 7/1998 | Beitler |
| 5,797,854 A | 8/1998 | Hedgecock |
| 5,800,350 A | 9/1998 | Coppleson et al. |
| 5,830,151 A | 11/1998 | Hadzic |
| 5,848,966 A | 12/1998 | Gusakov et al. |
| 5,851,191 A | 12/1998 | Gozani |
| 5,853,373 A | 12/1998 | Griffith et al. |
| 5,885,219 A | 3/1999 | Nightengale |
| 5,897,505 A | 4/1999 | Feinberg et al. ............. 600/547 |
| 5,904,712 A | 5/1999 | Axelgaard |
| 5,916,157 A * | 6/1999 | Crosz, Jr. ................... 600/372 |
| 5,916,159 A | 6/1999 | Kelly et al. |
| 5,916,179 A | 6/1999 | Sharrock |
| 5,928,158 A | 7/1999 | Aristides |
| 5,957,860 A | 9/1999 | Rodiera Olive |
| 5,961,484 A | 10/1999 | Gusakov et al. |
| 5,976,094 A | 11/1999 | Gozani |
| 5,984,102 A | 11/1999 | Tay |
| 5,991,649 A | 11/1999 | Garfield et al. |
| 6,023,631 A | 2/2000 | Cartmell et al. |
| 6,032,064 A | 2/2000 | Devlin et al. |
| 6,038,485 A | 3/2000 | Axelgaard |
| 6,044,294 A | 3/2000 | Mortzzavi et al. |
| 6,047,202 A | 4/2000 | Finneran et al. |
| 6,051,422 A | 4/2000 | Kovacs et al. |
| 6,055,448 A * | 4/2000 | Anderson et al. ............ 600/372 |
| 6,055,452 A | 4/2000 | Pearlman |
| 6,090,545 A | 7/2000 | Wohlstadter et al. |
| 6,115,623 A * | 9/2000 | McFee ........................ 600/372 |
| 6,132,386 A | 10/2000 | Gozani et al. |
| 6,132,387 A | 10/2000 | Gozani et al. |
| 6,146,335 A | 11/2000 | Gozani |
| 6,157,851 A * | 12/2000 | Kelly et al. .................. 600/386 |
| 6,173,198 B1 * | 1/2001 | Schulze et al. .............. 600/382 |
| 6,295,463 B1 * | 9/2001 | Stenzler ....................... 600/391 |
| 6,360,119 B1 | 3/2002 | Roberts |

\* cited by examiner

ELECTRODE ARRAY AND SKIN ATTACHMENT SYSTEM FOR NONINVASIVE NERVE LOCATION AND IMAGING DEVICE

TECHNICAL FIELD

This invention relates to a medical device for the noninvasive location and imaging of peripheral nerves. Specifically, the present invention is a sensor system for use at the skin surface comprising an electrode array assembly with multiple electrodes and a skin attachment system. Each electrode in the electrode array assembly maintains a connection to peripheral nerve detection and imaging instrumentation. A negative return wire is attached to the electrode array assembly and to a skin surface electrode during use of the sensor system. A disposable, sterile skin attachment system allows conductance between the electrode array and the skin surface of the subject. The skin attachment system contains individual hydrogel islands, each adapted to align accurately with a specific electrode of the electrode array. The layer of the skin attachment system that adheres to the skin surface of the subject may be left on the skin at the end of sampling to provide a skin marking guide. This facilitates the positioning of needles for subsequent nerve stimulation or therapy.

BACKGROUND OF THE INVENTION

The use of direct current skin surface conductance or resistance measurements has been employed in many forms for the identification of peripheral nerves, myofascial trigger points, and acupuncture points (Cory, et al., 1996; Kaslow and Lowenschuss, 1975; Kejariwal, et al., 1996; Kwok, et al., 1998; Lykken, 1971). An early example of this was the use of a transcutaneous electrical nerve stimulation (TENS) unit to identify acupuncture points. When a TENS unit is coupled between examiner and subject, the finger of the examiner acts as a sampling electrode (Kaslow and Lowenschuss, 1975). However, the literature in the field illustrates inconsistency in locating peripheral nervous tissue through electrical conductance measurements (Reichmanis et al., 1975).

U.S. Pat. No. 4,016,870 to Lock describes a system for acupuncture point location in which a single, hand-held probe of undisclosed composition is used to determine sites of high skin surface conductance. U.S. Pat. No. 5,897,505 to Feinberg, et al., describes a system for measuring selective tissue conductance and temperature utilizing chrome-plated, brass electrodes in a handheld embodiment. Although each of these systems measures conductance at the skin surface, they suffer two main drawbacks. First, metallic electrodes display uneven current densities at the skin surface-electrode interface, largely dependent on the underlying moisture pattern of the skin. Means for measuring skin surface conductance and resistance that do not employ aqueous interfaces are particularly subject to this effect (Cory, 1996; Freedman L W, 1994), and, in some cases, current densities became high enough to produce painful sensation. Second, handheld devices are subject to uncontrolled application pressures. This is complicated in larger diameter electrode systems, such as that of Feinberg, where the angle of application causes pressure to be unequally distributed on the skin surface. The use of electrical conductance measurements at the skin surface to locate nerve tissue is facilitated by the use of aqueous electrodes, rather than metallic or dry silver-silver chloride electrodes, and by the use of pulsed direct current as the device output, rather than alternating current (Kejariwal et al., 1996). Based upon observations such as these, a device that locates peripheral nerves transcutaneously was disclosed in U.S. Pat. No. 5,560,372 to Cory (the disclosure of which is incorporated herein by reference.)

The problem of avoiding metallic interfaces with the skin surface is addressed by the use of water-saturated felt electrodes in U.S. Pat. No. 5,560,372 to Cory and by the use of hydrogels (Jossinet and McAdams, 1990). The ability to obtain reproducible skin surface conductance and resistance readings allows the recognition of skin surface sites that correspond to underlying peripheral nerves (Cory, et al., 1996). While this approach circumvents the problems of current density disparities, of the formation of thin oxidation films on the electrodes, and of subsequent back electromotive force, additional problems remain that are associated with the interface between the sampling electrodes and the skin surface.

SUMMARY OF THE INVENTION

It is an object of the present invention to provide a sensor system comprising an electrode array and a skin attachment system for use with an electrical field generating device that can non-invasively detect peripheral nerves.

It is further an object of the present invention to provide a method for detecting peripheral nerves using the aforementioned sensor system.

It is further an object of the present invention to provide for an electrode array, which is flexible, reusable, and suitable for use in combination with a skin attachment system as herein described.

It is further an object of the present invention to provide for a skin attachment system, comprising hydrogel islands, which is disposable and suitable for use in combination with an electrode array as herein described.

Further objects and advantages of the invention will be apparent from the following description of the invention.

DETAILED DESCRIPTION OF THE INVENTION

The medical device of the present invention is a sensor system that comprises two components. A sensor system of the present invention thus comprises an electrode array and a skin attachment system. When combined to form the sensor system, both the electrode array and the skin attachment system are presented in the form of complementary arrays of electrodes and hydrogel islands, respectively. The electrode array comprises two or more electrodes, advantageously four or more electrodes. The electrodes may be arranged randomly, in a single line, or in another fixed order.

Advantageously, the electrodes of the array may be arranged in plural rows. The adjacent rows may be in line with one another or offset with respect to their nearest neighbor(s). A preferred arrangement is for the array to comprise a minimum of four electrodes arranged as two or more rows, where adjacent rows are in line with one another. Another preferred arrangement is for the array to comprise a minimum of four electrodes arranged as two or more rows of electrodes, where adjacent rows are offset with respect to one another.

A further preferred arrangement is for there to be a minimum of two rows of four or more electrodes each.

A further preferred arrangement is for there to be a minimum of two rows of eight or more electrodes each.

Another further preferred arrangement is for there to be a minimum of eight rows of eight electrodes each.

Figure 1:
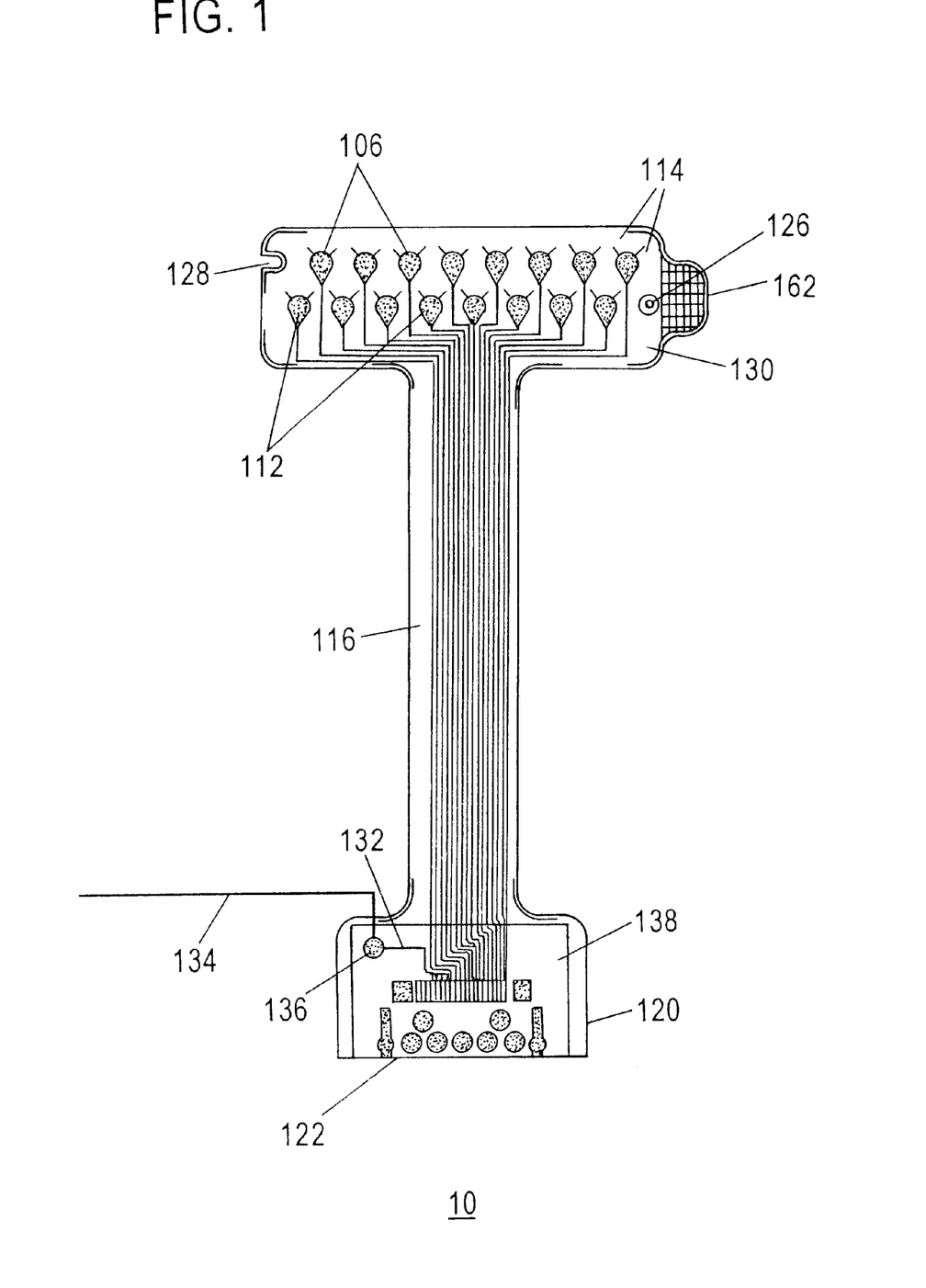
FIG. 1 is a basic depiction of an electrode array of the present invention in a 16-electrode conformation, view from side not facing skin (top view).
Figure 4:
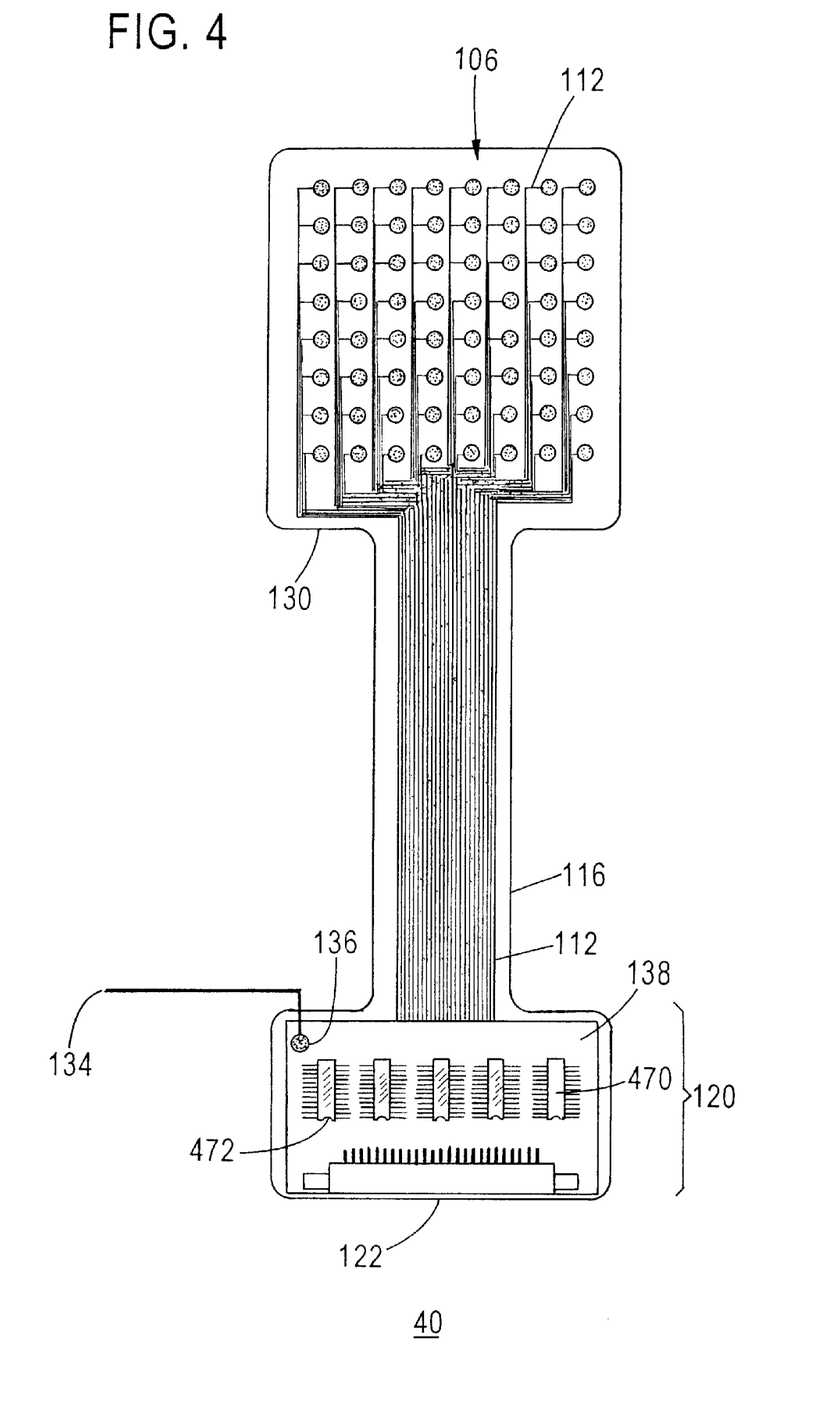
FIG. 4 shows an exemplary electrode array of the present invention in a 64-electrode conformation, top view.

An exemplary embodiment according to the present invention is a two row array, as depicted in FIG. 1, where an offset arrangement of adjacent rows is used. Another exemplary embodiment according to the present invention is an eight row arrangement, as depicted in FIG. 4, where adjacent rows are in line with one another.

By the foregoing, it should be apparent that any number of conformations is possible with this invention. The important consideration in constructing an electrode array assembly of the present invention is that the electrodes of the electrode array line up with the hydrogel islands of the skin attachment system so that they can operate together as the herein described sensor system.

An electrode array assembly of the present invention may advantageously be made flexible so that the electrode array assembly may conform to a wide variety of body surfaces, locations, and circumferences. To achieve this flexibility, the electrode array should comprise as a support structure a flexible, electrically non-conductive sheet. Also, it is useful to employ very thin, narrow metal paste as an electrical connection between the electrodes in the electrode array region and the leads in the electrical connector region of the electrode array.

The electrode array of the present invention may be reused, a feature which is particularly achieved when the electrode array is used with the separate skin attachment system of the present invention.

The electrode surface should be chemically, as well as biologically, inert. In other words, the electrode surface should not chemically react with, or be degraded by, surfaces which it will contact during normal use. To obtain reproducible measurements, the formation of thin, oxidation films on the electrode surface must be avoided. At the same time, the electrode array must be resistant to damage by bending and twisting. The electrode array must also be stable when cleaned with common sterilizing agents, such as isopropyl alcohol. The electrode array must also be stable upon sterilization by ethylene oxide, gamma radiation, or autoclaving.

In preparing the electrode array assemblies of the present invention, thought must be given to the reduction of sampling error. The present inventors have performed experiments to determine the size parameters that minimize sampling error. The present invention may be advantageously practiced by constructing electrode arrays in which the electrode diameters are in the range of about 2–3 mm, with edge-to-edge spacing of about 3 mm. Smaller electrode diameters and closer electrode spacing may result in excessive variation between sample readings. It is believed that, at smaller electrode diameters, hydrogel resistance increases due to decreasing cross-sectional area in relation to the electrical field path, which may introduce variation in sample readings. However, where such variations are tolerable, smaller electrode diameters may be used. Of course, larger electrode diameters and spacings may be advantageously employed and are contemplated as being within the scope of the present invention, although smaller diameters are generally preferred due to their generally more favorable resolution characteristics. The ordinary artisan will appreciate that a wide variety of electrode diameters and spacings may be used and are contemplated as being within the scope of the present invention.

The skin attachment system of the present invention provides an interface between the electrode array and the skin surface of a living being, preferably a mammal, more preferably a human patient. The skin attachment system comprises a plurality of layers. One layer, hereinafter the support layer, contains a plurality of hydrogel islands arranged in a support. Another layer, hereinafter the skin marking guide layer, is fenestrated (i.e. has holes) so that the hydrogel islands protrude through the holes therein. The support layer and the skin marking guide layer are held together by an adhesive that is easily broken, so that after imaging the peripheral nerves, the practioner may then peel the support layer away from the skin marking guide layer, leaving the latter attached to the skin.

The hydrogel may be any electrically conductive hydrogel known in the medicinal, biofeedback or biological testing arts.

The foam used in the support layer may be any foam known in the art for such applications. Particularly, preferred foams are closed cell foams.

The skin marking guide layer may be made of any polymeric material known in the medical arts. Particularly advantageous are those polymeric materials that are clear or translucent. The polymeric materials may be colored in order to enhance their visibility against skin. Particularly preferred are bright colors that offer enhanced contrast on any colored skin. Color such as blue and white are particularly preferred for the skin marking guide, however other colors, such a fluorescent yellow, orange, green and magenta may also be used.

The peripheral nerve imaging instrument to be employed is not critical to the present invention and may be any suitable instrument known in the art, such as the multiplexed system disclosed in U.S. Pat. No. 5,560,372, incorporated herein by reference.

The following non-limiting advantages may be realized by practicing this invention:

1. Sterility. The new skin attachment system directly contacts the skin of the subject and should be a sterile, disposable, adhesive patch. The electrode array, to which the skin attachment system adheres and which extends six inches away from the skin of the subject, may be cleansed with isopropyl alcohol or sterilized under ethylene oxide, gamma radiation, or autoclaving.

2. Skin marking. Once samples have been taken with the device, all but the bottom (skin marking guide) layer of the skin attachment system may be removed from the skin of the subject. This bottom layer is fenestrated, with holes that correspond to the location of the electrodes in the electrode array, and provides a skin marking guide. Skin can be marked through this skin marking guide to facilitate subsequent injection(s) at the site(s) chosen by the practitioner based upon the readings obtained, or the skin marking guide may be left in place on the skin to provide a convenient template for guiding a nerve stimulation needle or other needle.
3. Pressure applied to electrodes. The electrode array and skin attachment system, joined together, are placed on the skin surface before sampling and remain there by virtue of an adhesive on the skin side of the skin attachment system. This arrangement was designed in part to circumvent the possibility that unequal pressures applied to each of the electrodes by the practitioner would interfere with the readings obtained at sampling.
4. Motion artifacts. Stable adherence of the skin attachment system to the skin of the subject and to the electrode array decreases the possibility of motion artifacts.
5. Quality of image. The number of electrodes in the electrode array assembly may be increased in order to improve the resolution possible with the device.
6. Flexibility. The skin attachment system and electrode array may be manufactured with different numbers of electrodes in different arrangemeents to address multiple uses and user preferences. The remainder of the device remains standard.
7. Imaging of a two-dimensional area. To image a two-dimensional area, as required for neurodiagnostic applications of the device, the skin attachment system and electrode array may be manufactured in a two-dimensional rather than a linear format (for example, an 8×8 array). This circumvents the need to move the device along a line on the skin surface, which is cumbersome for the operator and subject to inaccuracy.
8. Parts replacement. The skin attachment system is disposable after each use, but is designed as a sterile part that is inexpensive to produce. The electrode arrays are reusable, but are subject to wear and tear during use and sterilization. This invention has the practical advantage of separating the electrode array from the rest of the device so that the electrode arrays may easily be replaced at minimal cost.
9. Operator's hands. The new invention offers an important practical advantage in freeing up the hands of the practitioner while samples are taken and displayed.
10. Acceptability in practice. The new invention significantly decreases the steps required to sample the skin surface, reducing the time required for nerve localization.
11. Size. The bulk of the device that is in proximity to the subject has been reduced significantly by this invention, facilitating use of the device and acceptance by the subject.
12. Placement of the negative return electrode. The attachment of a negative return electrode wire of limited length to the electrode array minimizes errors in the placement of the negative return electrode.

The ordinary artisan would appreciate that these considerations require selection of materials that possess the characteristics recited above. Such materials will be readily apparent and available to the skilled artisan who sets out to practice the invention as described herein.

Further uses, benefits and features of the present invention will be seen from a review of the detailed description of the preferred embodiments in conjunction with the various figures of the drawings.

PREFERRED EMBODIMENTS

An exemplary electrode array 10 according to the present invention is depicted in FIG. 1. The electrode array 10 has 16 electrodes 106, arranged in two rows, which are offset with respect to one another. Another electrode array 40 is depicted in FIG. 4. Electrode array 40 has 64 electrodes 106, arranged in eight rows and eight columns. Surfaces (not shown) of electrodes 106 are exposed through a nonconductive sheet (not shown) facing the skin surface (view not shown). The nonconductive sheet is advantageously a polyimide, however the composition of the nonconductive sheet need not be limited to this material. Other suitable nonconductive sheet materials include polycarbonates, polyurethanes, polyvinylchlorides, polybutylenes, etc.

The electrodes 106 are advantageously fabricated using a subtraction technique for production of printed circuit boards. An image of electrodes and traces is first developed on a copper-plated KAPTON® brand (duPont) polyimide polymer sheet. A photoresist layer is applied over the image. After exposure to ultraviolet radiation, the copper surrounding the photoresist protected regions is etched away with a ferric chloride solution. The photoresist is removed with an organic solvent, such as acetone. Following masking of the copper traces, nickel is electroplated onto the copper electrode pads. Gold is then electroplated onto the nickel electroplate. A final KAPTON® polyimide layer is laminated over the traces. Following soldering of the connector and integrated circuit elements, the electrode assembly is complete.

To ensure non-reactivity with a skin attachment system 30 (FIGS. 3A, 3B) or with a skin layer itself, the exposed surfaces of electrodes 106 are plated with gold in some embodiments according to the present invention. However, other conductive materials that do not readily react with skin are used in other embodiments according to the present invention. Such conductive materials include suitable metal alloys. Between the gold surfaces of electrodes 106 and underlying metal paste traces 112 is an interposed layer of nickel (not shown) to ensure adequate plating of the gold. Other interposed metal layers, e.g. tin, may be used. Opposite the gold-plated surface of the electrode the metal paste traces 114 in a Y-configuration provide stability and strength for the electrodes 106. The metal paste traces 112 extend from each electrode 106, through a stem 116 of the electrode array 10, 40, to attach to the instrumentation connector 122. The width and thickness of the metal paste traces 112 vary from 5–15 mil depending on the number of electrodes 106 in the array. For the larger, two-dimensional electrode arrays 40 (FIG. 4), integrated circuit elements consisting of shift registers 470 and multiplexers 472 are installed on the instrumentation connector portion 120 of the electrode array 40. In the embodiment depicted in FIG. 4, there is one shift register 470 and four multiplexers 472, however other configurations are possible and are contemplated as being within the general scope of the present invention.

The electrode arrays 10, 40 are wide at both the electrode sensor region 130 and the instrumentation connector region 120. Between the instrumentation connector region 120 and the electrode sensor region 130, the stem region 116 is narrow to promote flexibility and convenience of use. The electrode sensor region 130 of the electrode array 10 contains a registration hole 126 and a registration notch 128. These design characteristics allow for accurate positioning with the skin attachment system 30. A tab 162 is on one side of the electrode sensor portion 130 of the electrode array 10 for ease of removal of the electrode array 10 from a skin marking guide 308 (FIG. 3B) after sampling is complete. In some embodiments according to the present invention, the electrode arrays 10, 40 have one registration hole 126 and registration notch 128. In other embodiments according to the present invention, the number and position of the registration notches 128 and registration holes 126 vary, depending upon the dimensions of the sensor portion 130 of the electrode array 10, 40. Some larger two-dimensional electrode arrays employ additional registration elements. Others require no registration notches 128 or registration holes 126.

The instrumentation connector portion 120 of the electrode array 10, 40 has a plastic rigidizer 138 (which may made of any suitable material other than plastic) positioned on the side of the electrode array opposite the exposed electrodes. This rigidizer 138 provides additional support for the instrumentation connector 122 and any attached integrated circuit elements such as shift registers 470 and multiplexers 472. A negative return lead 134 connects via a soldered union 136 to a metal trace 132 running to the instrumentation connector 122. The instrumentation connector portion 120 of the electrode array 10, 40 is encapsulated in molded medicinal grade silicone polymer or polyethylene. In some embodiments according to the present invention, metal paste material is applied at points of curvature and stress on the electrode array 10, 40 to provide additional shear-resistance and prolong the useable life span of the electrode array.

Figure 2:
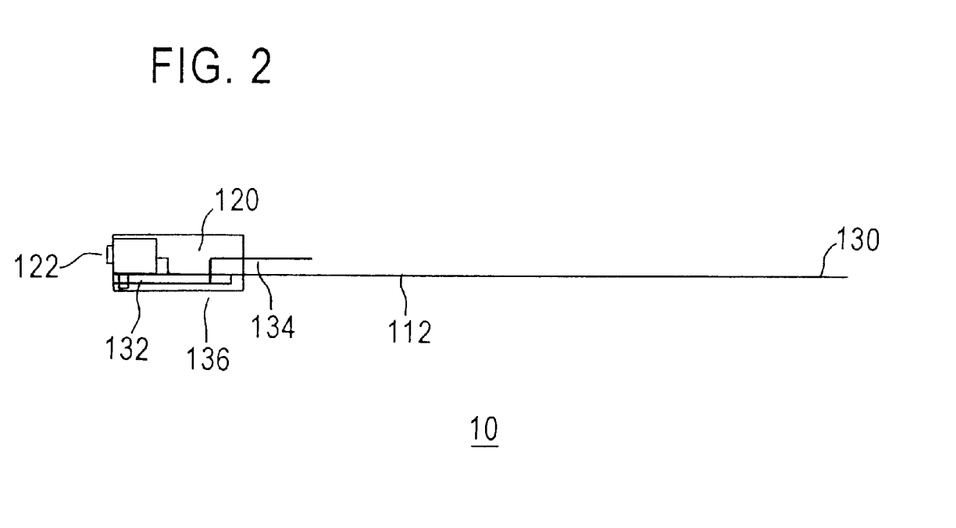
FIG. 2 is a cross-sectional side view of an electrode array of the present invention in a 16-electrode conformation.

FIG. 2 depicts a side cross-sectional view of the electrical components of the embodiment depicted in FIG. 1. Within the instrumentation connector region 120 is instrumentation connector 122, which connects to metal paste traces 112. The negative return electrode wire 134 is connected to instrumentation connector 122 through metal paste trace 132 at soldered union 136. The metal paste traces 112 connect to the electrode sensor region 130.

Figure 3A:
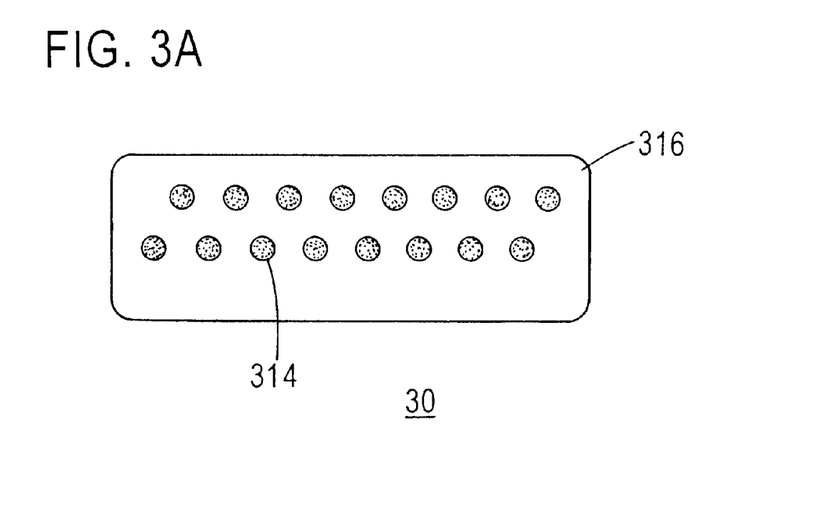
FIG. 3A shows a skin attachment system in a 16-electrode conformation, top view.
Figure 3B:
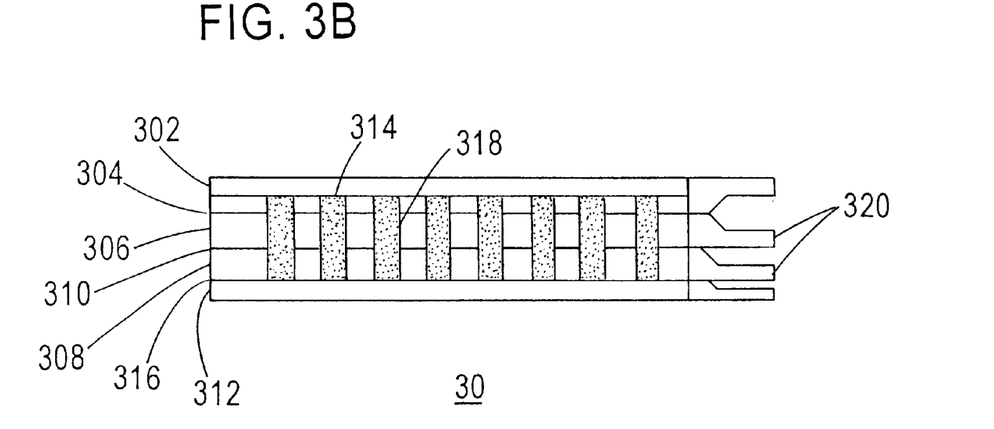
FIG. 3B shows a skin attachment system in a 16-electrode conformation, side view.

Skin attachment systems. An embodiment of a skin attachment system 30 for use with an electrode array 10 as depicted in FIG. 1 is depicted in FIGS. 3A and 3B. Skin attachment system 30 is shaped to conform exactly to a particular electrode array configuration such as electrode array 10 in FIG. 1. A suitable skin attachment system 30 according to the present invention consists of seven layers:

1. Top cover 302 of the skin attachment system 30 is composed of polyethylene, polystyrene, polyvinylchloride, polybutylene, polyurethane or other material and provides protection for the underlying materials.
2. A top adhesive layer 304 allows solid connection of the skin attachment system 30 with the electrode array 10. The top adhesive layer 304 does not extend over conductive hydrogel islands 314.
3. Beneath the top adhesive layer 304 is a support layer 306 comprised of, but not limited in composition to, closed-cell foam. The thickness of the support layer 306 may be varied depending on the application intended.
4. Between the support layer 306 and a skin marking guide 308 is an intermediate adhesive layer 310, which joins the support layer 306 and the skin marking guide 308.
5. The skin marking guide 308 is formed of a material such as 4 mil polyethylene, colored so as to be easily visible on all skin types (e.g., blue or white).
6. A bottom adhesive layer 316 allows the skin marking guide 308, and thus the entire skin attachment system with the electrode array 10 on top of it, to adhere to the skin of the subject. The skin marking guide 308 allows the skin to be marked at site(s) of interest before its removal.

Holes 314 are formed through all layers of the skin attachment system 30 except for the top cover 302 and the bottom cover 312. The holes 314 are filled with a conductive material 318 comprising, but not limited in composition to, an organic hydrogel. Registration elements are positioned on the skin attachment system to provide for accurate placement of the electrode array 10 on the skin attachment system 30. Tabs 320, aligned with the electrode array tab 162 of electrode array 10, are found on the support layer 306 and the skin marking guide 308. The tabs 320 aid in removal of the support layer 306 and skin marking guide 308. In some embodiments, the skin attachment system 30 is packaged in a rigid container or aluminized pouch (not shown) which is sealed in an airtight fashion. The skin attachment system 30, in its container, is capable of withstanding sterilization by gamma-irradiation. In its sealed container, the skin attachment system 30 has a shelf life of approximately 18 months.

Figure 5A:
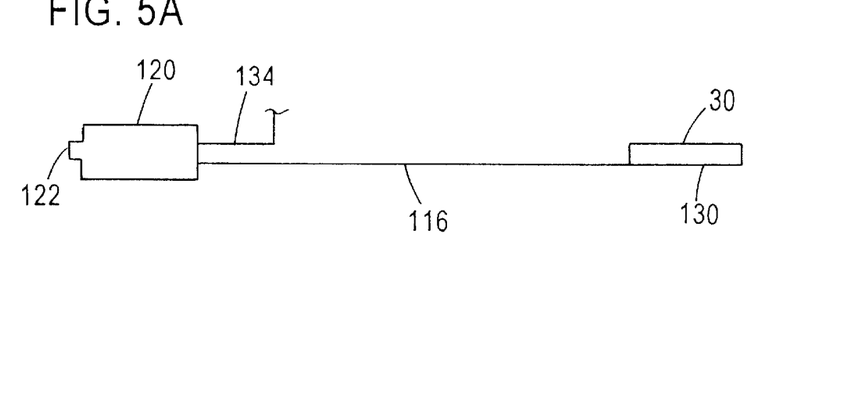
FIG. 5A shows an assembly of an electrode array and a skin attachment system according the present invention, side view.
Figure 5B:
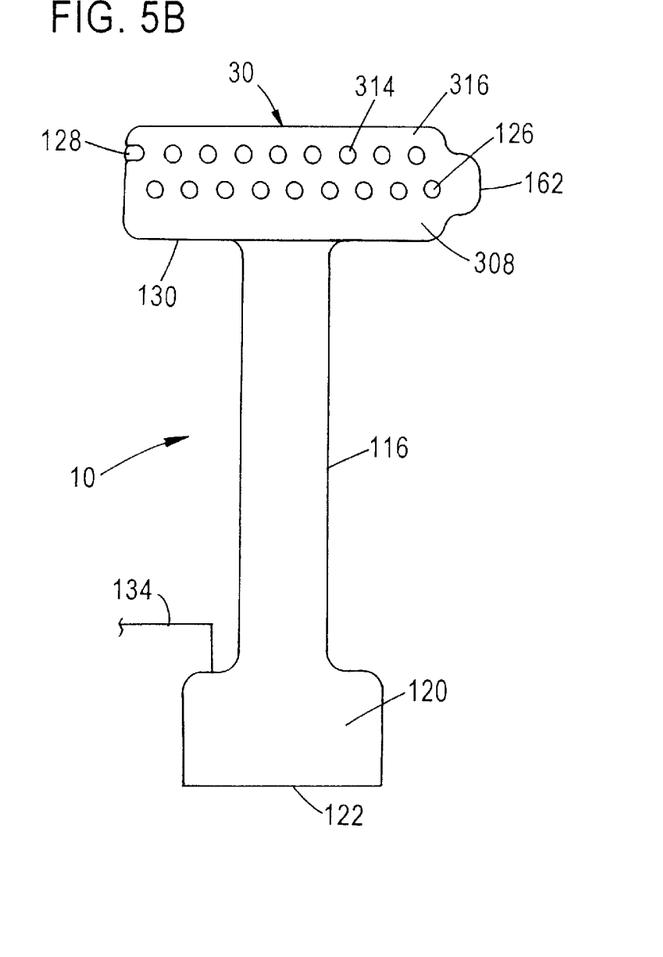
FIG. 5B shows an assembly of an electrode array and skin attachment system of FIG. 5A, view from the skin attachment side.

A combination of skin attachment system 30 and electrode array 10 is shown in FIGS. 5A and 5B. In FIG. 5A Skin attachment system 30 is applied to electrode sensor region 130 of electrode array 10. In FIG. 5B, the electrode array 10 and skin attachment system 30 are seen from the side facing the skin during attachment. The skin attachment system 30 is seen after bottom cover 312 has been peeled off. Visible are registration notch 128, registration hole 126, tab 162, conductive hydrogel islands 314 and adhesive layer 316, which covers skin marking guide 308. Negative return lead 134 connects to instrumentation connector region 120, which has an instrumentation connector 122 for connection to an appropriate instrument.

An electrode array and skin attachment system according to the present invention, when connected to an appropriate nerve location device, is used to identify peripheral nerves, neuromas, myofascial trigger points, nerve entrapments, and acupuncture points. To use the invention, one attaches the skin attachment system 30 to an appropriately configured electrode array 10, which is then connected to the nerve location device (not part of this invention).

Figure 6:
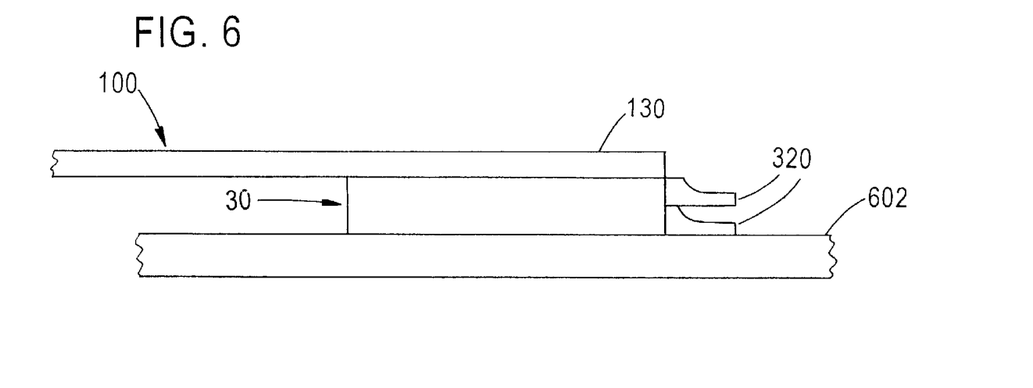
FIG. 6 shows a side view of an electrode array and skin attachment system according to the present invention attached to an area of skin.

FIG. 6 depicts an embodiment according to the present invention, wherein the skin attachment system 30 is then attached to skin 602. Electrode array 10 has been attached to the skin attachment system 30, from which top layer 302 and bottom layer 312 have been removed.

Figure 7A:
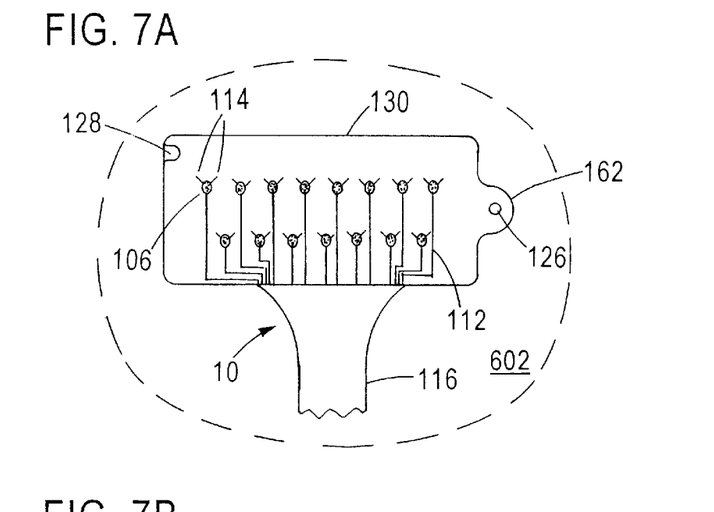
FIGS. 7A–7D illustrate the steps of removing an electrode array from a skin marking guide according to the present invention, marking a location on an area of skin through a hole in the skin marking guide, and removal of the skin marking guide from the area of skin.

A method of using the electrode array 10 and skin attachment system 30 according to the present invention is depicted in FIGS. 7A–7D. In FIG. 7A, an electrode array 10 is shown as it is attached to skin 602 through a skin attachment system (not shown). Visible in this view is the electrode sensor region 130 of the electrode array 10, which comprises electrodes 106, metal paste traces 112, 114, registration notch 128, registration hole 126 and tab 162. The electrode sensor region 130 is attached to the instrumentation connector region (not shown) through stem 116.

Figure 7B:
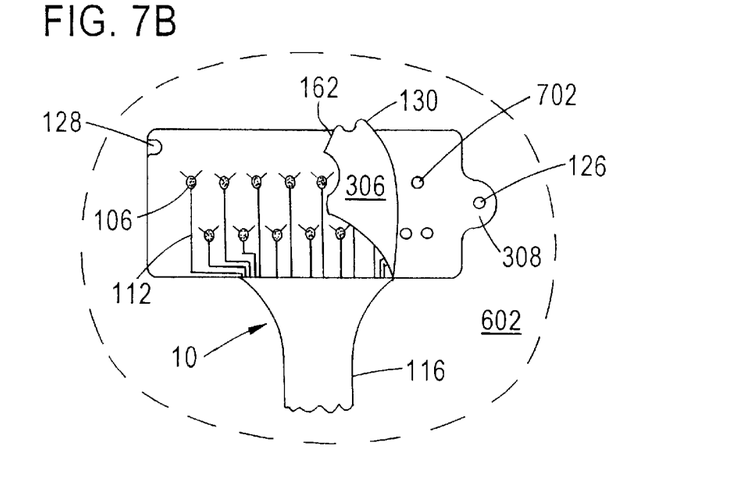

FIG. 7B depicts removal of electrode array 10 from skin marking guide 308. The support layer 306 goes with electrode array 10 as it is peeled back from the skin marking guide 308 via tab 162.

Figure 7C:
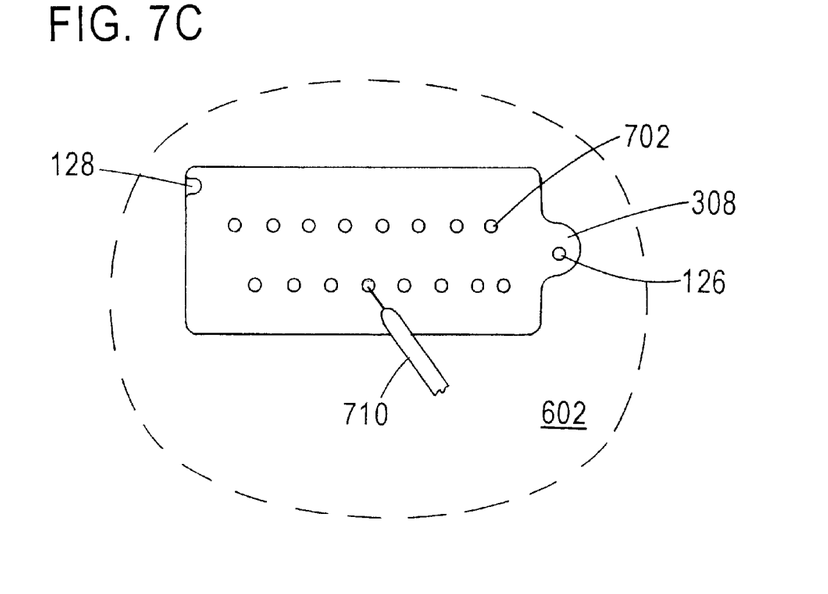

FIG. 7C depicts marking of skin 602 through a hole 702 in skin marking guide 308 with a pen 710.

Figure 7D:
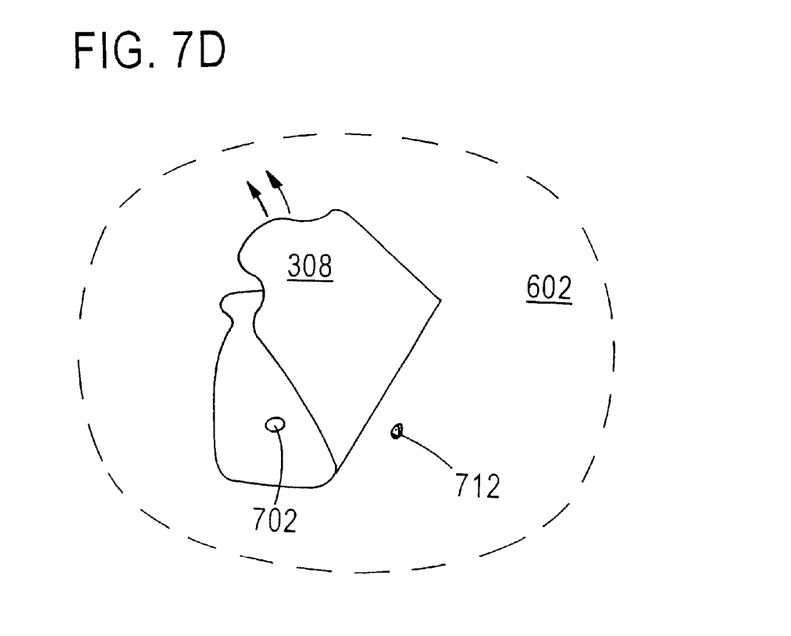

FIG. 7D depicts peeling away of skin marking guide 308 from skin 602 to reveal mark 712.

Steps for carrying out a method of using an electrode array and skin attachment system according to the present invention include the following.

1. Connect the electrode array 10 to an instrumentation connector (not shown) of a nerve location device.
2. Remove the top cover 302 from the electrode array side of the skin attachment system 30.
3. Aligning the registration features of skin attachment system 30 with the registration notch 128 and the registration hole 126 of electrode array 10, position and securely attach the skin attachment system 30 to the electrode array 10.
4. Remove bottom cover 312 from skin surface side of the skin attachment system 30.
5. Attach the skin marking guide 308, now on the combined electrode array and skin attachment system, to dry, intact skin of a suitable subject. The skin is advantageously prepared by stripping 3–5 times with adhesive tape.
6. Attach the negative return electrode (standard ECG electrode) (not shown) to the skin of subject within 10–20 cm of the electrode array assembly 10.
7. Attach the negative return electrode wire 134, for instance with an alligator clip, to the negative return electrode of the instrument (not shown).
8. Obtain samples with the nerve location instrument (not shown).
9. Once skin surface has been sampled with the nerve location device, there are two options:
   a. Using the tab 162 on the electrode array 10 and the tab(s) 320 on the skin attachment system 30, remove the entire electrode array 10 and the skin attachment system 30 from skin surface, or
   b. Using the tabs 320 on the skin attachment system 30 as an aid, remove all but the skin marking guide 308 from the skin surface. At this point, one may mark the skin through the skin marking guide 308 at the point(s) of interest determined by the nerve location device. Once the skin surface has been marked, the skin marking guide 308 is removed and the skin surface prepared for positioning of a nerve stimulation needle and/or a needle for therapeutic injection (e.g., regional anesthesia or pain relief).
10. All portions of the skin attachment system 30 are discarded.
11. The electrode array 10 is cleansed with isopropyl alcohol or, if desired, may be sterilized under ethylene oxide, gamma radiation, or autoclaving. The latter method may decrease the longevity of the electrode array.

While the foregoing preferred embodiments serve to illustrate the present invention and the best mode of operation thereof, other suitable embodiments, arrangements and uses may be envisioned by the ordinary artisan and as such are contemplated as being within the scope of the herein described invention.

What is claimed is:

1. An electrode array comprising:
   a sheet of electrically non-conductive material having a sensor electrode region, an instrumentation connector region and a flexible stem region mechanically joining the sensor electrode region and the instrumentation connector region;
   circuitry comprising an electrode array having at least two electrodes, which are disposed within the sensor electrode region,
   a connection lead corresponding to each electrode disposed within the instrumentation connector region,
   a negative return lead disposed within the instrumentation connector region,
   an electrically conductive connection between each electrode and its corresponding connection lead; and
   registration features on the sensor electrode region for a unique alignment with a skin attachment system.

2. An electrode array of claim 1, wherein the electrode array has 16 electrodes.

3. An electrode array of claim 1, wherein the electrode array has 64 electrodes.

4. An electrode array of claim 1, wherein the electrode array comprises at least four electrodes arranged in rows.

5. An electrode array of claim 4, wherein the sensor electrodes of each row are in line with the electrodes of the adjacent row or rows.

6. An electrode array of claim 5, wherein the electrode array comprises 64 electrodes arranged in 8 rows of 8 sensor electrodes each.

7. An electrode array of claim 4, wherein the sensor electrodes of each row are offset with respect to the sensor electrodes of the adjacent row or rows.

8. An electrode array of claim 7, wherein the sensor array has 16 electrodes arranged in two rows of 8 sensor electrodes each.

9. An electrode array of claim 1, wherein the sheet of electrically non-conductive material is a sheet of polyimide.

10. An electrode array of claim 1, wherein the sensor electrodes are gold-plated.

11. An electrode array of claim 1, wherein the sensor electrodes are connected to the connector leads by metal paste conductive traces, which are printed or silk-screened onto the electrically non-conductive sheet.

12. An electrode array of claim 1, wherein the circuitry further comprises integrated circuitry chips.

13. An electrode array of claim 1, further comprising metal paste reinforcement.

14. A skin attachment system for attaching an electrode array to skin comprising:
   at least one registration feature for alignment of the skin attachment system with an electrode array;
   a skin marking guide layer, having at least two marking holes therein;
   a support layer having one hydrogel island hole corresponding to each marking hole in the skin marking guide layer, each said hydrogel island hole containing a hydrogel island, which projects into its corresponding marking hole;
   wherein the skin marking guide layer and the support layer are detachably affixed one to the other.

15. A skin attachment system of claim 14, further comprising a top cover layer adjacent to the top of the support layer, a fenestrated skin marking guide layer adjacent the bottom of the support layer and a bottom cover layer adjacent the fenestrated skin marking guide;
   the top cover layer being detachably affixed to the support layer; and
   the fenestrated skin marking guide layer being detachably affixed to the bottom cover layer and detachably affixed to the support layer;
   so that the top cover layer and the bottom cover layer may be removed from the skin attachment system prior to using the skin attachment system for imaging peripheral nerves.

16. A sensor system for the imaging of peripheral nerves, comprising a skin attachment system, an electrode array and a medical imaging instrument,
   said skin attachment system for attaching an electrode array to skin comprising:
   at least one registration feature for alignment of the skin attachment system with an electrode array;

a skin marking guide layer, having at least two marking holes therein;

a support layer having one hydrogel island hole corresponding to each marking hole in the skin marking guide layer, each said hydrogel island hole containing a hydrogel island, which projects into its corresponding marking hole;

wherein the skin marking guide layer and the support layer are detachably affixed one to the other; and said electrode array comprising:

a sheet of electrically non-conductive material having a sensor electrode region, an instrumentation connector region and a flexible stem region mechanically joining the electrode sensor region and the instrumentation connector region;

circuitry comprising an electrode array having at least two electrodes, which are disposed within the sensor electrode region, a connection lead corresponding to each electrode disposed within the instrumentation connector region, a negative return lead disposed within the instrumentation connector region, an electrically conductive connection between each electrode and its corresponding connection lead; and registration features on the sensor electrode region for alignment with a skin attachment system.

17. A sensor system of claim 16, further wherein the skin attachment system further comprises a top cover layer adjacent to the support layer, a fenestrated skin marking guide layer adjacent to the support layer and a bottom cover layer adjacent to the fenestrated skin marking guide layer;

the top cover layer being detachably affixed to the support layer; and the fenestrated skin marking guide layer being detachably affixed to the bottom cover layer and detachably affixed to the support layer;

so that the top cover layer and the bottom cover layer may be removed from the skin attachment system prior using the skin attachment system for imaging peripheral nerves.

18. A method of using a sensor system of claim 16, comprising connecting the electrode array to a medical imaging instrument;

lining up the registration features of the skin attachment system with those of the electrode array and connecting the skin attachment system to the electrode array;

attaching the skin attachment system to skin;

attaching the negative return lead to skin.

19. A method of claim 18, further comprising removing the support layer and hydrogel islands from the skin marking guide layer, leaving the latter attached to the skin as a skin marking guide;

marking the skin through the marking holes of the skin marking guide or leaving the skin marking guide in place as a template for directing the position of at least one needle.

20. An electrode array of claim 1, wherein the electrode array contains electrodes having diameters of 2 mm to 3 mm.

21. An electrode array of claim 1, wherein the electrode array contain electrodes having an edge to edge spacing of about 3 mm.

* * * * *

UNITED STATES PATENT AND TRADEMARK OFFICE
CERTIFICATE OF CORRECTION

PATENT NO.     : 6,564,079 B1           Page 1 of 1
DATED          : May 13, 2003
INVENTOR(S)    : Philip C. Cory et al.

It is certified that error appears in the above-identified patent and that said Letters Patent is hereby corrected as shown below:

<u>Title page,</u>
Item [73], Assignee, change "MO" with -- MT--

Signed and Sealed this

Twenty-eighth Day of October, 2003

JAMES E. ROGAN
*Director of the United States Patent and Trademark Office*